(12) United States Patent
Laufer (10) Patent No.: US 8,226,671 B2
(45) Date of Patent: Jul. 24, 2012

(54) METHODS AND DEVICES FOR PROVIDING DIRECTION TO SURGICAL TOOLS

(75) Inventor: Michael D. Laufer, Menlo Park, CA (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 534 days.

(21) Appl. No.: 12/427,850

(22) Filed: Apr. 22, 2009

(65) Prior Publication Data

US 2009/0264902 A1  Oct. 22, 2009

Related U.S. Application Data

(60) Provisional application No. 61/047,078, filed on Apr. 22, 2008.

(51) Int. Cl.
*A61F 11/00* (2006.01)
*A61F 2/00* (2006.01)
*A61F 13/00* (2006.01)
*A61B 17/00* (2006.01)
*A61B 17/50* (2006.01)
*A61M 5/178* (2006.01)

(52) U.S. Cl. ........ 606/157; 606/108; 606/139; 606/151; 600/37; 600/585; 604/170.03

(58) Field of Classification Search .................. 600/585, 600/37; 606/108, 109, 139–150, 151, 157, 606/158; 604/19, 22, 93.01, 158–162, 164, 604/170.03, 264, 272, 523
See application file for complete search history.

(56) References Cited

U.S. PATENT DOCUMENTS

| 5,074,868 A | 12/1991 | Kuzmak |
| 5,159,446 A | 10/1992 | Hibino et al. |
| 5,449,368 A | 9/1995 | Kuzmak |
| 6,071,292 A * | 6/2000 | Makower et al. ............. 606/158 |
| 6,494,888 B1 | 12/2002 | Laufer et al. |

(Continued)

FOREIGN PATENT DOCUMENTS

WO  WO-2007064906 A2   6/2007

OTHER PUBLICATIONS

International Search Report & Written Opinion, PCT/US2009/014362, Mailed Jun. 8, 2009, 11 pages.

(Continued)

*Primary Examiner* — Max Hindenburg
*Assistant Examiner* — John Pani
(74) *Attorney, Agent, or Firm* — Nutter McClennen & Fish LLP (57) ABSTRACT

Methods and devices are provided for providing direction to surgical tools. In one embodiment, a surgical device can include a cannulated elongate shaft with a cannulated curved distal tip. The device can be configured to be introduced into a body of a patient, and one portion of the device can be configured to be positioned on a proximal side of a tissue wall and a distal-most portion of the device including at least a portion of the curved distal tip can be configured to be positioned on the other, distal side of the tissue wall. A surgical tool can be configured to be advanced through the device to pass the surgical tool through the tissue wall with the curved distal tip providing direction for the surgical tool.

4 Claims, 4 Drawing Sheets

U.S. PATENT DOCUMENTS

| | | |
|---|---|---|
| 6,572,629 B2 | 6/2003 | Kalloo et al. |
| 6,663,639 B1 | 12/2003 | Laufer et al. |
| 6,676,674 B1 | 1/2004 | Dudai |
| 6,966,875 B1 | 11/2005 | Longobardi |
| 6,976,969 B2 | 12/2005 | Messerly |
| 7,347,863 B2 | 3/2008 | Rothe et al. |
| 7,841,347 B2 | 11/2010 | Sonnenschein et al. |
| 8,034,062 B2 | 10/2011 | Laufer et al. |
| 8,092,474 B2 * | 1/2012 | Laufer et al. .................. 606/157 |
| 2001/0049497 A1 | 12/2001 | Kalloo et al. |
| 2002/0022851 A1 | 2/2002 | Kalloo et al. |
| 2002/0169464 A1 | 11/2002 | Latour |
| 2003/0208212 A1 | 11/2003 | Cigaina |
| 2004/0102804 A1 | 5/2004 | Chin |
| 2004/0225305 A1 | 11/2004 | Ewers et al. |
| 2005/0075652 A1 | 4/2005 | Byrum et al. |
| 2005/0261712 A1 | 11/2005 | Balbierz et al. |
| 2005/0277963 A1 | 12/2005 | Fields |
| 2005/0283235 A1 | 12/2005 | Kugler et al. |
| 2006/0178564 A1 | 8/2006 | Jones et al. |
| 2006/0241653 A1 | 10/2006 | Jones et al. |
| 2006/0252983 A1 | 11/2006 | Lembo et al. |
| 2007/0015956 A1 | 1/2007 | Crawford et al. |
| 2007/0038239 A1 | 2/2007 | Ritchie |
| 2007/0218083 A1 | 9/2007 | Brooks |
| 2008/0208216 A1 * | 8/2008 | Cerier .......................... 606/139 |
| 2008/0319435 A1 | 12/2008 | Rioux et al. |
| 2009/0005797 A1 | 1/2009 | Laufer et al. |
| 2009/0018391 A1 | 1/2009 | Laufer et al. |
| 2009/0264910 A1 | 10/2009 | Laufer |

OTHER PUBLICATIONS

International Search Report & Written Opinion, PCT/US2009/041362, Mailed Oct. 26, 2010, 8 pages.

International Search Report & Written Opinion, PCT/US2009/041369, Mailed Oct. 26, 2010, 7 pages.

International Search Report (PCT/US2009/041369) dated Jun. 16, 2009.

* cited by examiner

METHODS AND DEVICES FOR PROVIDING DIRECTION TO SURGICAL TOOLS

CROSS REFERENCE TO RELATED APPLICATIONS

The present application claims the priority of U.S. Provisional Application Ser. No. 61/047,078 filed Apr. 22, 2008 entitled "Device For Placement Of A Circumferential Band Around A Bodily Organ Through A Natural Orifice," which is hereby incorporated by reference in its entirety.

FIELD OF THE INVENTION

The present invention relates to methods and devices for providing direction to surgical tools.

BACKGROUND OF THE INVENTION

Laparoscopic surgery has greatly reduced the size and scope of incisions made in a patient and resulted in reduced morbidity and mortality rates. However, even with the reductions in the size and extent of incisions as a result of laparoscopic surgery, complications in and during surgical procedures remain. A technique that is developing to further reduce surgical complications is to work through a natural orifice such as the mouth, to access the stomach, where a hole is made through the stomach wall, to gain access to the inside of the abdominal space outside of the stomach. This NOTES approach, or natural orifice transenteric surgery, allows scarless surgical procedures with faster recovery, fewer complications, and less pain.

Stomach tissue often needs surgical treatment to treat fistulas and to close trans-gastric incisions to stop stomach fluids from leaking from the stomach to surrounding tissue and to stop infectious matter from spreading from or to the stomach tissue. Other stomach treatments include stomach reduction procedures for obese patients. Traditionally, physicians have placed devices laparoscopically on the external surface of the gastric wall to create a restricted stomach capacity, such as restricting or gastric bands. Another traditional procedure for stomach reduction includes a laparoscopic procedure in which surgeons protrude into the abdomen from the exterior of the patient and staple the stomach into a smaller volume. This restriction creates a pouch inside the stomach which fills quickly when food is ingested and assists in generating a sensation of being full. However, these procedures have drawbacks such as complications from port punctures of the stomach, large incisions, substantial recovery time, expense, lost productive work time, infection, and the like. Further, the one or more incisions required by the current surgical procedures including laparoscopy, include a morbidity and mortality rate that can be reduced by reducing or eliminating the need for an incision by approaching the surgical site through endoluminal procedures.

Thus, there is a need for devices and methods which allow surgical procedures to be performed laparoscopically while reducing or eliminating the need for an incision.

SUMMARY OF THE INVENTION

The present invention generally provides methods and devices for providing direction to surgical tools, particularly to a distal end of a surgical tool when it is positioned in a patient and located remote from a surgeon or other operator of the tool. In one embodiment, a surgical device is provided that includes an elongate member having a curved distal tip configured to be positioned in an opening in a tissue wall, and a proximal control mechanism configured to manipulate the curved distal tip to change a position of the curved distal tip relative to the tissue wall at least when the curved distal tip is positioned in the opening.

The curved distal tip can have any number of variations. For example, the curved distal tip can have a fixed degree of curvature, can be tapered, and/or can be cannulated. For another example, the curved distal tip can be configured to be positioned in the opening with a proximal portion of the curved distal tip substantially perpendicular to the tissue wall and with a distal portion of the curved distal tip curving toward a surface of the tissue wall.

The device can vary in any other number of ways. For example, the device can include a second elongate member having a second curved distal tip configured to be positioned in a second opening in a tissue wall. The proximal control mechanism can be configured to manipulate the second curved distal tip to change a position of the second curved distal tip relative to the tissue wall at least when the second curved distal tip is positioned in the second opening. For another example, the elongate member can be cannulated. For another example, the device can include an overtube having an inner passageway extending therethrough, the elongate member being configured to extend along a sidewall of the overtube with the curved distal tip extending distally beyond a distal end of the overtube. Rotation of the overtube around a longitudinal axis of the overtube with the elongate member extending along the sidewall of the overtube and the curved distal tip extending distally beyond the distal end of the overtube can be effective to change an effective length of the curved distal tip. In some embodiments, the device can include a guide wire configured to be advanced along the curved distal tip.

In another aspect, a surgical method is provided. In one embodiment, the method includes advancing an elongate member having a curved distal tip into a body of a patient, positioning the elongate member through an opening formed in a tissue wall in the body of the patient with a first portion of the elongate member extending proximal to the tissue wall and with a second portion of the elongate member that includes at least a portion of the curved distal tip extending distal to the tissue wall, and advancing a surgical tool along the curved distal tip to guide the surgical tool distal to the opening in a curved direction.

The method can vary in any number of ways. For example, the method can include advancing a second elongate member having a second curved distal tip into the body of the patient, positioning the second elongate member through a second opening formed in the tissue wall in the body of the patient with a first portion of the second elongate member extending proximal to the tissue wall and with a second portion of the second elongate member that includes at least a portion of the second curved distal tip extending distal to the tissue wall, and advancing the surgical tool from the curved distal tip to be positioned along the second curved distal tip. For another example, positioning the elongate member through the opening can include manipulating a control mechanism coupled to the elongate member to change a distance between the curved distal tip and the tissue wall. For another example, advancing the elongate member into the body of the patient can include advancing an overtube having the elongate member coupled to a sidewall of the overtube into the body of the patient. Rotating the overtube around a longitudinal axis of the overtube with the elongate member positioned through the opening can change a distance between the curved distal tip and the tissue wall. For yet another example, advancing the surgical tool along the curved distal tip can include advancing a guide wire along the curved distal tip. In some embodiments, the method can include forming the opening in the tissue wall with the guide wire.

In another embodiment, a surgical method is provided that includes advancing a guide element having a curved distal tip into a hollow body organ, e.g., a stomach, an intestine, or an esophagus, positioning the guide element through an opening formed through a wall of the body organ with a proximal portion of the guide element positioned inside the body organ and a distal portion of the guide element outside the body organ with the curved distal tip curving along at least a portion of an outer surface of the body organ, and advancing a surgical tool along the curved distal tip to guide the surgical tool along the outer surface of the body organ. The method can have any number of variations. For example, the method can include advancing the surgical tool along a perimeter of the body organ and advancing the surgical tool through the wall of the body organ to position first and second lengths of the surgical tool inside the body organ with a third length of the surgical tool between the first and second lengths extending at least partially around the perimeter of the body organ. The method can also include advancing a restriction over the third length of the surgical tool to position the restriction band at least partially around the perimeter of the body organ. For another example, in some embodiments, the guide element can include an elongate tubular body, and advancing the surgical tool along the curved distal tip can include advancing the surgical tool through the elongate tubular body. For yet another example, positioning the guide element through the opening can include manipulating a control mechanism to change an angle that the distal portion of the curved distal tip curves toward the outer surface of the body organ.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary methods and devices are provided for providing direction to surgical tools. In general, the methods and devices can help direct a surgical tool in an arced path, especially when a distal end of the device is remote from a proximal end that is controlled by a surgeon or other operator. In one embodiment, a surgical device can include a cannulated elongate shaft with a cannulated curved distal tip. The device can be configured to be introduced into a body of a patient, and one portion of the device can be configured to be positioned on a proximal side of a tissue wall and a distalmost portion of the device including at least a portion of the curved distal tip can be configured to be positioned on the other, distal side of the tissue wall. A surgical tool, e.g., a guide wire, a guide tube, a grasper, a cutting instrument, etc., can be configured to be advanced through the device to pass the surgical tool through the tissue wall. The curved distal tip can be configured to guide the surgical tool in a curved direction on the distal side of the tissue wall, e.g., in a direction not perpendicular to a distal surface of the tissue wall, which can facilitate desirable positioning of the surgical tool on the distal side of a tissue wall with no or limited visualization of the distal side of the tissue wall. The curved distal tip can also be configured to guide the surgical tool toward or along the distal surface of the tissue wall without a grasper or other additional surgical tool having to manipulate the surgical tool on the distal side of the tissue wall.

A person skilled in the art will appreciate that while the methods and devices are described in connection with endoscopic procedures in which the surgical instruments are delivered through a natural orifice, the methods and devices disclosed herein can be used in numerous surgical procedures and with numerous surgical instruments. By way of non-limiting example, the devices can be used in laparoscopic procedures, in which the device is introduced percutaneously. The methods and devices can also be used in open surgical procedures. A person skilled in the art will also appreciate that the methods and devices disclosed herein can be used with any surgical tool, such as a scoping device, having a cannula or other working channel through which the shaft of a surgical instrument can be advanced and that is configured to be inserted into a body, such as through a natural orifice, through a puncture hole formed in tissue, and in any other way appreciated by a person skilled in the art. Non-limiting examples of a scoping device include an endoscope, a laparoscope, and a colonoscope.

The devices discussed herein can be made from any combination of rigid and/or flexible materials, but in an exemplary embodiment the materials are biocompatible. A person skilled in the art will appreciate that the term "flexible" as used herein is intended to encompass a variety of configurations and generally refers to a property that enables a material or an object to deform to some extent without failing. In an exemplary embodiment, the device or at least portions thereof are composed of at least one biocompatible and flexible material, e.g., plastic, titanium, stainless steel, a shape memory material, etc.

Figure 1:
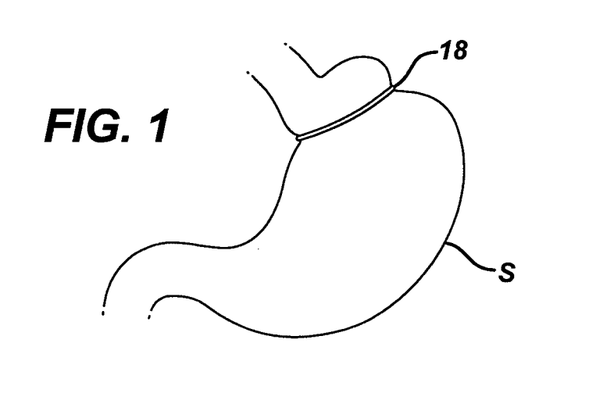
FIG. 1 is a side view of a stomach having one embodiment of a restriction band deployed thereon.

In an exemplary embodiment, an implant device can be configured to be implanted onto a lumen of a hollow body organ or conduit including the stomach, the intestine, the heart, the airway, the vein, the artery, the esophagus, the aorta, and/or the renal artery without creating an incision outside the body, wherein the implant can be configured and/or adjusted to constrict or reduce the stomach or other hollow body organ or conduit. An exemplary embodiment is shown in FIG. 1, wherein a band 18 is deployed around a patient's stomach S.

In an exemplary embodiment of a surgical procedure such as in deploying the band 18, an instrument such as an endoscope can be delivered into the stomach through the mouth or other natural orifice, a hole can be made through the stomach, a flexible wire or tube can be directed at least partially around the outside of the stomach and re-enter the stomach at or near the point of the original exit from the stomach. Suitable non-limiting embodiments of endoscopic devices including tissue manipulating functionality are described in more detail in U.S. Pat. No. 6,494,888 entitled "Tissue Reconfiguration" issued Dec. 17, 2002 and U.S. Pat. No. 6,663,639 entitled "Methods And Devices For Tissue Reconfiguration" issued Dec. 16, 2003, which are hereby incorporated by reference in their entireties. The tissue hole can be made by cutting, piercing, burning with radiofrequency (RF) energy directed into the tissue through a conductive tip on the wire or needle knife, or similar method as will be appreciated by a person skilled in the art. In some embodiments, a guide wire device can be used to form the hole. Although this exemplary embodiment is discussed with respect to the stomach, a person skilled in the art will appreciate that the methods and devices disclosed herein are equally applicable to other organs and/or conduits.

Figure 2A:
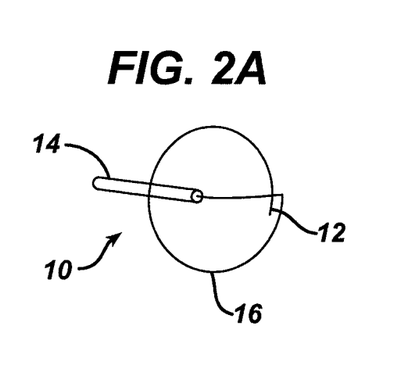
FIG. 2A is a perspective view of one embodiment of a guide wire device.
Figure 2B:
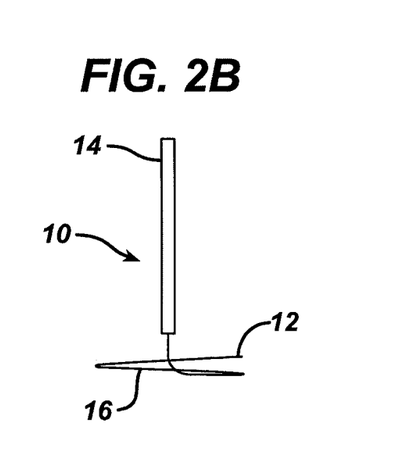
FIG. 2B is another perspective view of the guide wire device of FIG. 2A.

An exemplary embodiment of a guide wire device 10 is shown in FIGS. 2A and 2B. The guide wire device 10 has a distal tip 12 that can be energized with RF energy, sharpened, or otherwise configured to puncture a tissue wall of a hollow body organ or conduit from inside the hollow organ. By manipulating a proximal handle 14 of the device 10, a guide wire 16 of the guide wire device 10 can be moved through and outside the wall of the organ or conduit around the organ or conduit as illustrated in one embodiment in FIG. 3 in which the wire 16 is shown positioned around an outer surface of the patient's stomach S along at least a portion of a perimeter of the stomach S with first and second lengths of the wire 16 inside the stomach S and a third length of the wire 16 between the first and second lengths extending at least partially around the perimeter of the stomach S. Throughout such a procedure, the user manipulable, proximal end of the handle 14 can remain outside of the patient's mouth or other natural body orifice, e.g., through an endoscopic device as mentioned above.

Figure 3:
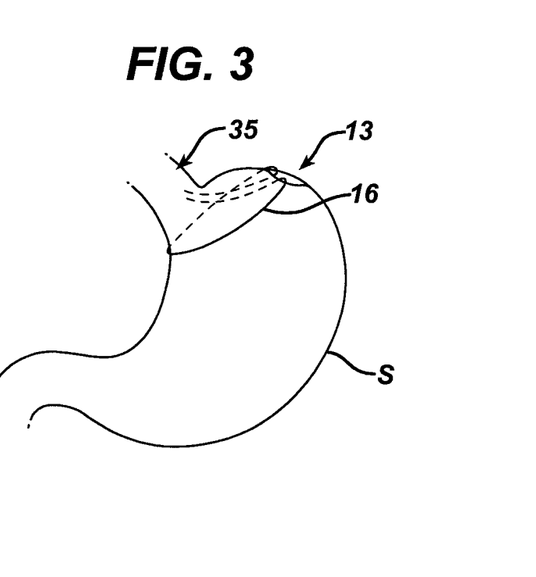
FIG. 3 is a side partially transparent view of one embodiment of a guide wire positioned around a stomach.

The guide wire 16 can encounter resistance or encounter tissue through which it must pass as it traverses through a body of a patient. In that case, the wire 16 can be rotated, vibrated axially at audible or sub-ultrasonic frequencies to act similarly to a jack-hammer but at a much smaller scale, and/or flexed in one direction and then another at some frequency in order to make passage possible. Various embodiments of a guide wire that can be rotated, vibrated, and/or flexed to help dissect tissue are described in more detail in U.S. patent application Ser. No. 12/427,853 entitled "Methods And Devices For Dissecting Tissue" filed on even date herewith, which is hereby incorporated by reference in its entirety.

Figure 2C:
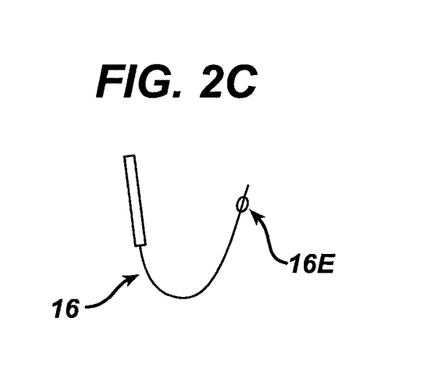
FIG. 2C is a perspective view of one embodiment of a guide wire device having a distal expansion member in the form of a balloon.

The guide wire can optionally be configured with a tip that allows axial expansion for passage through tissue. This dissection may be accomplished through expanding an expandable member such as a balloon 16E on a guide wire 16', as illustrated in one embodiment in FIG. 2C, in order to create a space to loosen the tissue, deflating the balloon 16E and advancing the guide wire 16', re-expanding the balloon 16E, and repeating as often as necessary to accomplish passage. Alternatively, the tip of the guide wire can have a scissor-like member, where the scissor-like member can be configured to be opened and closed while the guide wire is pushed or advanced distally, in order to accomplish passage. Various embodiments of a guide wire having a distal scissor-like member are described in more detail in previously mentioned U.S. patent application Ser. No. 12/427,853 entitled "Methods And Devices For Dissecting Tissue" filed on even date herewith.

Figure 4A:
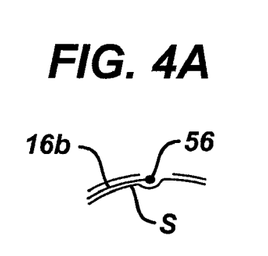
FIG. 4A is a partial cross-sectional side view of one embodiment of a guide wire having a distal bump tip being advanced along a tissue wall of a stomach.
Figure 4B:
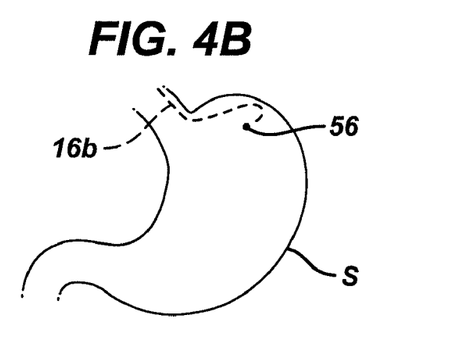
FIG. 4B is a side partially transparent view of the guide wire of FIG. 4A being advanced around the stomach.

FIGS. 4A and 4B show another embodiment of a guide wire 16b that includes a distal bump tip 56. In this embodiment, the bump tip 56 can be advanced around the stomach S from the inside, pushed with a peristalsis-like motion.

Figure 5A:
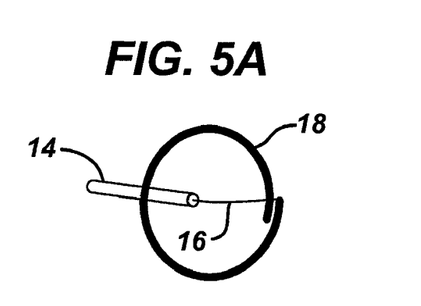
FIG. 5A is a perspective view of one embodiment of a restriction band placed over the guide wire device of FIGS. 2A and 2B.
Figure 5B:
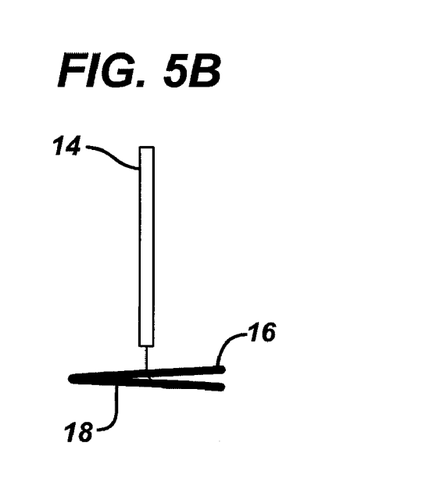
FIG. 5B is another perspective view of the restriction band of FIG. 5A placed over the guide wire device of FIGS. 2A and 2B.

Once the guide wire 16 is placed around at least a portion of the hollow body organ or conduit, a restricting band 18 can be advanced thereover as shown in one embodiment in FIGS. 5A and 5B. Alternatively, a guide tube first can be extended over the guide wire 16 and the restricting band 18 deployed either inside or outside the guide tube. In some embodiments, a restricting band can be placed around a body organ or conduit directly without the need for an additional guide wire or tube, which can be integrated into the band.

Figure 6:
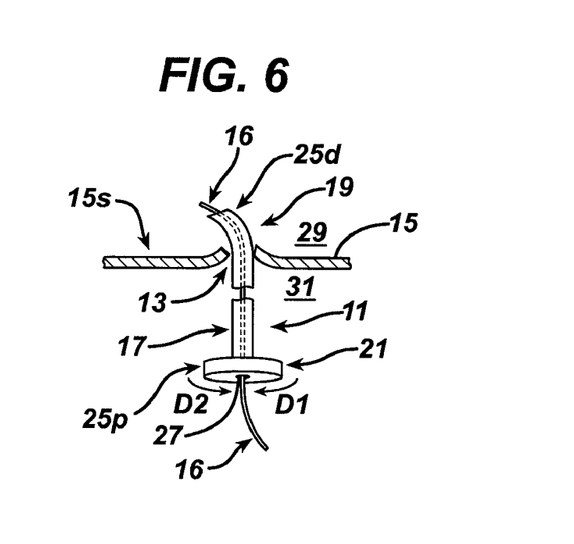
FIG. 6 is a side partial cross-sectional, partial transparent view of one embodiment of a device having a curved distal tip guiding a guide wire through an opening formed in a tissue wall.

An exemplary device 11 configured to help to guide at least one surgical tool around a hollow body organ or conduit is illustrated in FIG. 6, in which it is positioned through an opening 13 in a tissue wall 15, e.g., a wall of the body organ or conduit. A person skilled in the art will appreciate that the device 11 can be configured to guide at least one surgical tool in an arcuate path around a hollow body organ or conduit as illustrated, within a hollow body organ or conduit, and/or around any other body tissue. Generally, the guide device 11 can include a guide element in the form of an elongate member, elongate shaft, or elongate body 17 having a curved distal tip 19 configured to be positioned in the opening 13 in the tissue wall 15. The device 11 can also include a proximal control mechanism, e.g., a handle 21, configured to facilitate manipulation of the device 11 from outside a body of a patient. At least when the curved distal tip 19 is positioned in the tissue wall opening 13, the handle 21 or other proximal control mechanism can be configured to manipulate the curved distal tip 19 to change a position of the curved distal tip 19 relative to the tissue wall 15 as discussed further below.

An inner passageway or lumen 27 can longitudinally extend through at least a portion of the device 11, such as longitudinally extending between a distal-most end 25d and a proximal-most end 25p of the device 11 as shown in FIG. 6 such that the device 11 including the elongate body 17 and the curved distal tip 19 can be cannulated. The inner passageway 27 can have any size and shape, e.g., cylindrically-shaped, configured to allow at least one surgical tool, e.g., the guide wire 16, the band 18, a grasper, a cutting instruments, etc., to be slidably disposed therein. A person skilled in the art will appreciate that the term "grasper" as used herein is intended to encompass any surgical instrument that is configured to grab and/or attach to tissue and thereby manipulate the tissue, e.g., forceps, retractors, movable jaws, magnets, adhesives, stay sutures, etc. A person skilled in the art will also appreciate that the term "cutting instrument" as used herein is intended to encompass any surgical instrument that is configured to cut tissue, e.g., a scalpel, a harmonic scalpel, a blunt dissector, a cautery tool configured to cut tissue, scissors, an endoscopic linear cutter, a surgical stapler, etc.

The device 11 can be formed from any combination of rigid and/or flexible materials. In an exemplary embodiment, the elongate body 17 can be flexible to help allow the elongate body 17 to be inserted into a body of a patient, e.g., through a tortuous pathway such as the esophagus or other body lumen, the curved distal tip 19 can be rigid to help facilitate arcuate guidance of surgical tools as discussed further below, and the handle 21 can be rigid to help ease manipulation of the device 11.

The handle 21 is illustrated in this embodiment as being located at a proximal-most end of the elongate body 17, but the handle 21 can be located anywhere at the elongate body's proximal end. The handle 21 can be, for non-limiting example, a substantially cylindrical disc or knob as shown, although as will be appreciated by a person skilled in the art the handle 21 can have any size, shape, and configuration that allows the device 11 to be held outside the body of a patient. The illustrated disc or knob shape of the handle 21 can allow the handle 21 to be manipulated using one hand, which can free the other hand for other surgical tasks. The handle 21 can be held and manipulated to help insert at least the curved distal tip 19 into a patient, rotate at least the curved distal tip 19 within the patient, and remove the device 11 from the patient. The passageway 27 can extend through the handle 21 to allow one or more surgical tools, e.g., the guide wire 16, to be slidably disposed therein. A diameter of the passageway 27 can therefore be smaller than a diameter of the handle 21. In some embodiments, such as if the handle is configured as a grippable handhold extending at a non-zero angle from one or more discrete locations around a perimeter of the elongate body 17, the passageway 27 can be separate from the handle. The diameter of the handle 21 can also be larger than a diameter of the elongate body 17, which can help the handle 21 serve as a stop mechanism configured to prevent the device 11 from being fully distally advanced into a body of a patient through an opening used to insert a distal portion of the device 11 into the patient's body. The passageway 27, the handle 21, and the elongate body 17 can share a central longitudinal axis, as shown in this illustrated embodiment, which can help more predictably position at least a portion of the curved distal tip 19 through an opening in tissue. A person skilled in the art will appreciate that while the handle 21 can make the device 11 easier to manipulate, the device 11 need not include the handle 21 but instead be manipulated using another proximal control mechanism, e.g., a proximal end of the elongate body 17, etc.

The elongate body 17 can be substantially cylindrical-shaped, as shown, although the elongate body 17 can have any shape. The elongate body 17 can also have any size, e.g., a diameter of about ¾ inches, such that its longitudinal length can allow at least a portion of the device 11 to be inserted into a body of a patient with at least a portion of the handle 21 being located outside the patient. The elongate body 17 can be integrally formed with or otherwise fixedly attached to the curved distal tip 19 as shown in this embodiment, although in some embodiments the curved distal tip 19 can be removably coupled to the elongate body 17. As will be appreciated by a person skilled in the art, any attachment mechanism can be used to removably couple the elongate body 17 and the curved distal tip 19, e.g., complementary threads, a snap fit, etc.

The curved distal tip 19 can have a variety of sizes, shapes, and configurations. As illustrated in this embodiment, the curved distal tip 19 can include a cannulated distal portion of the device 11 having a fixed degree of curvature. In some embodiments, the curved distal tip's degree of curvature can be variable or controllable between a plurality of fixed degrees of curvature, e.g., through use of snake-like coil or bendable links. The curved distal tip 19 can have any degree of curvature, such as in a range of about 0° to 90°. The curved distal tip 19 can optionally include a distally tapered distal-most end, e.g., at the distal end 25d of the device 11, as illustrated in this embodiment, which can help ease insertion of the curved distal tip 19 through tissue and/or help expand or dilate the tissue opening 13 through which the curved distal tip 19 can be advanced.

Figure 7:
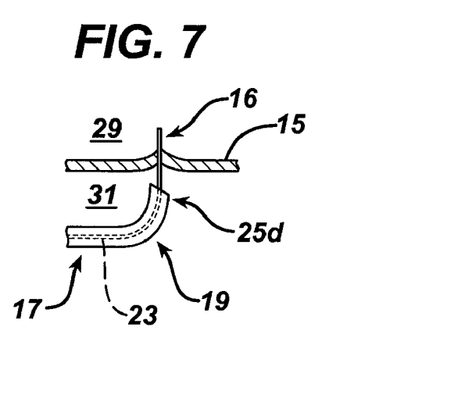
FIG. 7 is a side partial cross-sectional, partial transparent view of the guide wire of FIG. 6 forming the opening in the tissue wall.

In use, the device 11 can be positioned within the opening 13 in a variety of ways. In an exemplary embodiment, as shown in FIG. 7, at least the curved distal tip 19 of the device 11 can be distally advanced into an internal cavity 31 of a hollow body organ or conduit. At least a distal portion of the elongate body 17 can also be advanced into the internal cavity 31. A surgical tool configured to penetrate tissue, e.g., the guide wire 16 or other cutting instrument, can be advanced through the passageway 23, either before or after at least a portion of the device 11 has been advanced into the internal cavity 31, and advanced distally beyond the device's distal end 25d to penetrate the tissue wall 15. The guide wire 16 or other tool used to penetrate the wall 15 can penetrate through the tissue wall 15 as shown in FIG. 7 and advance into the body cavity 29 to form the opening 13 through the wall 15, although in some embodiments the guide wire 16 or other tool used to penetrate the wall 15 can penetrate a partial distance through the wall 15 with the curved distal tip 19 and/or other surgical tool penetrating a remaining distance through the wall 15.

Figure 8:
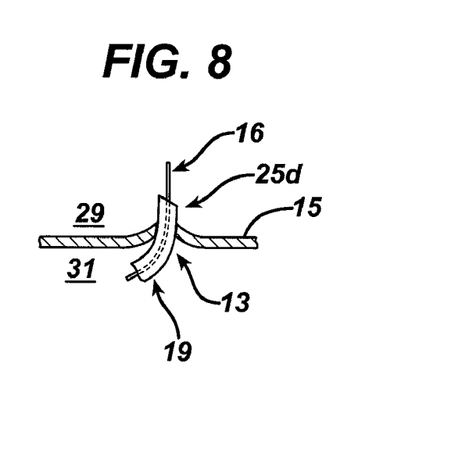
FIG. 8 is a side partial cross-sectional, partial transparent view of the guide wire and the curved distal tip of FIG. 6 advancing through the opening in the tissue wall.

Regardless of how the opening 13 through the wall 15 is formed, the curved distal tip 19 can be advanced through the opening 13, as illustrated in one embodiment in FIG. 8. The curved distal tip 19 can have a diameter greater than a diameter of the one or more surgical tools used to form the opening 13 and can thus expand or dilate the opening 13 as the curved distal tip 19 distally advances therethrough. Orientation of the curved distal tip 19 relative to the wall 15 can be adjusted by, e.g., rotating the device 11 by rotating the handle 21 in a clockwise direction D1 and/or a counterclockwise direction D2. A scoping device (not shown) can be positioned in the body of the patient to help visualize orientation of the curved distal tip 19 relative to the wall 15. The scoping device can be positioned within the internal cavity 31, such as by being advanced transorally through the esophagus, or outside the internal cavity, such as by being advanced through a percutaneous abdominal access port or opening. The guide wire 16 can optionally have a light at a distal end thereof to facilitate visualization directly with a scoping device or indirectly through a tissue wall and to facilitate positioning of the curved distal tip 19 and the guide wire 16 extending therethrough, such as described in more detail in U.S. Patent Publication No. 2009/0005797 entitled "Methods And Devices For Placement Of An Intra-Abdominal Or Intra-Thoracic Appliance Through A Natural Body Orifice" filed Apr. 22, 2008 and U.S. Patent Publication No. 2009/0018391 entitled "Methods And Devices For Placement Of An Intra-Abdominal Or Intra-Thoracic Appliance Through A Natural Body Orifice" filed Apr. 22, 2008, which are hereby incorporated by reference in their entireties.

With the device 11 positioned within the opening 13, any portion of the device 11 can be positioned within the body cavity 29 distal to the wall 15, and any portion of the device 11 can be positioned within the internal cavity 31 proximal to the wall 15. As in the illustrated exemplary embodiment, the curved distal tip 19 can have a first position in the wall 15, as shown in FIG. 8, in which the curved distal tip 19 can be substantially perpendicular to the wall 15 on both sides of the wall 15, e.g., in the body cavity 29 and in the internal cavity 31, such that a surgical tool advanced through the passageway 23 in the curved distal tip 19 can also extend substantially perpendicular to the wall 15 on both sides of the wall 15. The curved distal tip 19 can be distally advanced through the opening 13 to move from the first position to a second position, shown in FIG. 6, in which a proximal portion of the curved distal tip 19 can be positioned within the internal cavity 31 substantially perpendicular to the tissue wall 15 and a distal portion of the curved distal tip 15 can be positioned within the body cavity 19 such that the curved distal tip 15 curves toward a distal or outer surface 15s of the tissue wall 15. In this way, the guide wire 16 and/or any other surgical tool advanced through the curved distal tip 19 positioned in the second position in the tissue wall 15 can be directed along the outer surface 15s of the wall 15. In this way, the guide wire 16 and/or any other surgical tool advanced through the curved distal tip 19 can be distally advanced through the passageway 23, advanced distally beyond the distal end 25d of the device 11, and move in a curved direction. If the curved distal tip 19 has a degree of curvature of about 90°, the guide wire 16 and/or any other surgical tool advanced through the curved distal tip 19 can be advanced substantially parallel to the wall's outer surface 15s.

The guide wire 16 and/or any other surgical tool advanced through the curved distal tip 19 can be advanced any distance along the outer surface 15s of the wall 15 to extend any distance around a perimeter of the wall 15. In one embodiment, the guide wire 16 can be advanced around a perimeter of the wall 15 and reenter the internal cavity 31 through the opening 13 in the wall 15, with or without the device 11 positioned in the opening 13 to help guide the guide wire 13 through the tissue wall 15. The device 11 can be removed from the opening 13, e.g., by proximally moving the device 11, thereby leaving the guide wire 16 in position around the stomach S, as illustrated in FIG. 3 with terminal ends of the guide wire 16 extending into the internal cavity 31 of the stomach S and/or into the patient's esophagus 35. As mentioned above, once the guide wire 16 is placed around at least a portion of the stomach S, an appliance can be advanced thereover with or without use of a guide tube, e.g., to place the appliance around the stomach S, e.g., similar to the restricting band 18 positioned around the stomach S as shown in FIG. 1.

Figure 9:
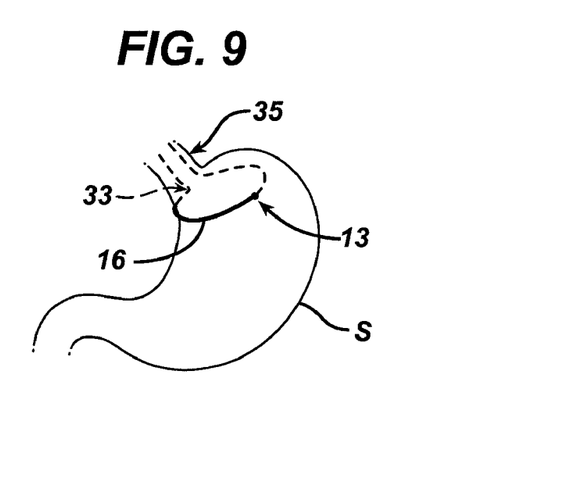
FIG. 9 is a side partial transparent view of the guide wire of FIG. 6 advanced around a partial perimeter of a stomach.
Figure 10:
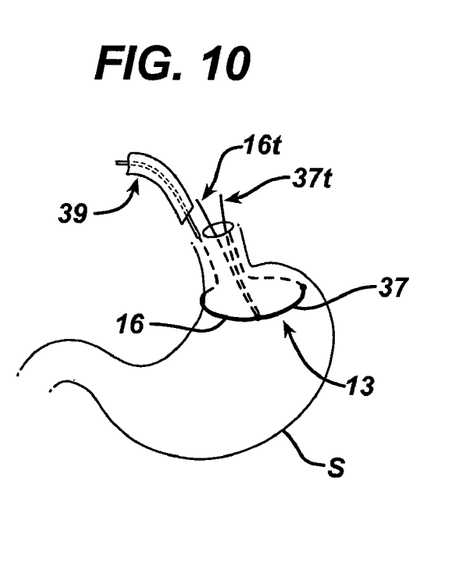
FIG. 10 is a side partial transparent view of the guide wire of FIG. 9 and a second guide wire each advanced around partial perimeters of the stomach.

In another exemplary embodiment, illustrated in FIG. 9, the guide wire 16 can be advanced through the curved distal tip 19 (not shown in FIG. 9) positioned in the opening 13 a partial distance along the wall's outer surface 15s around the perimeter of the wall 15 and reenter the internal cavity 31 through a second opening 33 formed in the tissue wall 15, e.g., about 180° away from the opening 13, with terminal ends of the guide wire 16 extending into the internal cavity 31 of the stomach S and/or into the patient's esophagus 35. In this way, first and second lengths of the guide wire 16 can be positioned inside the stomach S with a third length of the guide wire 16 between the first and second lengths extending partially around the perimeter of the stomach S. As will be appreciated by a person skilled in the art, the second opening 33 can be formed in the tissue wall 15 in any way, e.g., using a distal end of the guide wire 16 to penetrate through the wall 15. The device 11 can be removed from the opening 13, by proximally moving the device 11, thereby leaving the guide wire 16 in position around a partial circumference of the stomach S as shown in FIG. 9. Optionally, to position a guide wire around a circumference of the stomach S, a second guide wire 37 can be positioned around the outer surface 15s of the wall 15 as shown in FIG. 10. The second guide wire 37 can be advanced into the stomach S in any way and be advanced out of the internal cavity 31 through one of the openings 13, 33, advanced around at least a partial perimeter of the stomach S, e.g., around an opposite side of the stomach S from the other guide wire 16, and advanced into the internal cavity 31 through the other one of the openings 13, 33. Terminal ends of the guide wires 16, 37 extending into the internal cavity 31 through the same opening, e.g., terminal ends 16t, 37t advanced through the opening 13, can be tied, crimped, or otherwise joined together, thereby securely positioning a guide wire including the two guide wires 16, 37 around a circumference of the stomach S. An appliance 39, e.g., a gastric band, can be advanced over the guide wire including the two guide wires 16, 37 to be positioned around the stomach S, e.g., similar to the restricting band 18 positioned around the stomach S as shown in FIG. 1.

The device 11 can optionally be mounted to a control mechanism in the form of an overtube configured to help facilitate handling and positioning of the device 11 and/or to help introduce one or more additional surgical instruments, e.g., a scoping device, a cutting instrument, etc., into the body of a patient through an inner passageway of the overtube. As shown in one exemplary embodiment in FIG. 11, the device 11 can be mounted to a sidewall 41s of an overtube 41. In an exemplary embodiment, at least a portion of the elongate body 17 of the device 11 can be mounted within the overtube's sidewall 41s with the handle 21 of the device 11 positioned proximal to a proximal end 41p of the overtube 41 and the curved distal tip 19 of the device 11 positioned distal to a distal end 41d of the overtube 41. In an exemplary embodiment, the device 11 can be rotatably disposed in a passageway longitudinally extending through the sidewall 41s. A person skilled in the art will appreciate that the device 11 can be movably or fixedly mounted to the sidewall 41s of the overtube 41 in any number of ways, e.g., attached to an interior or exterior surface of the sidewall 41s using an attachment mechanism such as an adhesive, slidably extending along a longitudinal channel formed in the sidewall 41s, etc.

Figure 11:
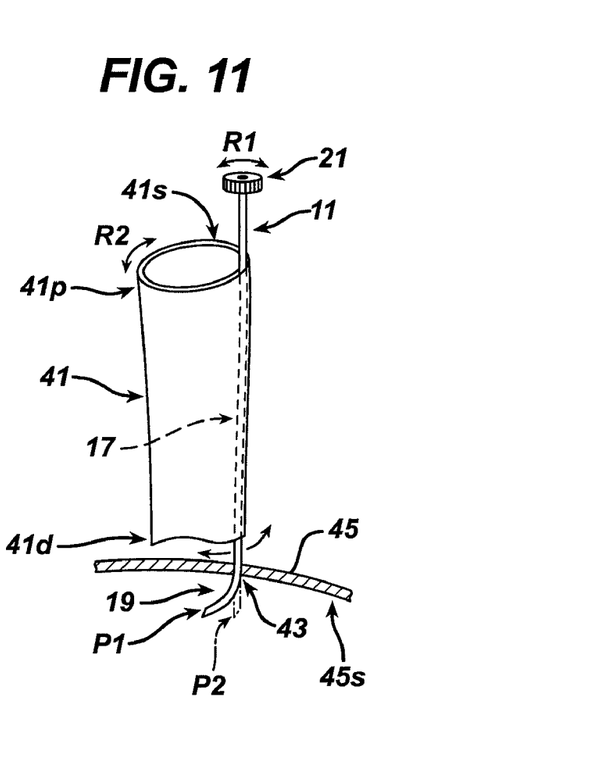
FIG. 11 is a side partial cross-sectional, partial transparent view of the device of FIG. 6 with the curved distal tip advanced through a tissue wall and the device mounted to one embodiment of an overtube.

With the device 11 mounted to the overtube 41, the device 11 can be configured to be rotated relative to the overtube 41 around a longitudinal axis of the device 11, e.g., by rotating the handle 21 as shown by directional arrow R1. Alternatively or additionally, the overtube 41 can be configured to be rotated around a longitudinal axis of the overtube 41, e.g., by rotating the overtube 41 as shown by directional arrow R2.

Figure 12:
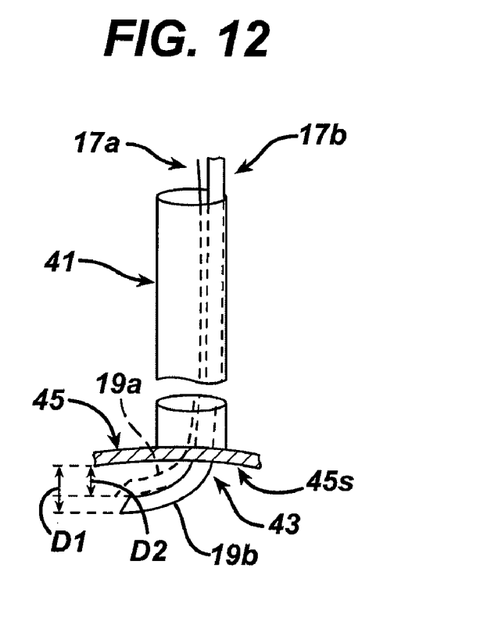
FIG. 12 is a side partial cross-sectional, partial transparent view of the device and overtube of FIG. 11 showing first and second rotational positions of the overtube.

In use, the curved distal tip 19 can be advanced through an opening 43 formed in a tissue wall 45, similar to that discussed above. In an exemplary embodiment, the device 11 can be mounted to the overtube 41 when the curved distal tip 19 advances through the opening 43. Rotation of the device 11 relative to the overtube 41 and the tissue wall 45 and/or rotation of the overtube 41 relative to the tissue wall 45 when the curved distal tip 19 is positioned in the opening 43 as illustrated in FIGS. 11 and 12 can help change a distance between the curved distal tip 19 and a distal surface of the tissue and/or change an angle that the curved distal tip 19 curves toward the distal surface of the tissue, e.g., to change an effective length of the curved distal tip 19 to push the curved distal tip 19 further through wall 45 and/or control a distance of a surgical tool advanced through the curved distal tip 19 from an outer surface 45s of the tissue wall 45. For non-limiting example, as shown in FIG. 11, rotation of the device 11 relative to the overtube 41 with the curved distal tip 19 positioned in the tissue 45 can orient the curved distal tip 19 from a first position P1 to a second position P2 having a different orientation relative to the wall 45, which can help better direct a surgical tool, e.g., a guide wire, advanced through the curved distal tip 19. For another non-limiting example, as illustrated in FIG. 12, rotation of the overtube 41 relative to the tissue 45 can move the device 11 from a first position, e.g., with the elongate body 17a and the curved distal tip 19a in a first position with the curved distal tip 19a a first distance D1 from the outer surface 45s of the wall 45, to a second position, e.g., with the elongate body 17b and the curved distal tip 19b in a second position with the curved distal tip 19b a second distance D2 from the outer surface 45s of the wall 45 that is greater than the first distance D1. The device 11 and/or the overtube 41 can be rotated in any number of directions any number of times to position the device 11.

Figure 13:
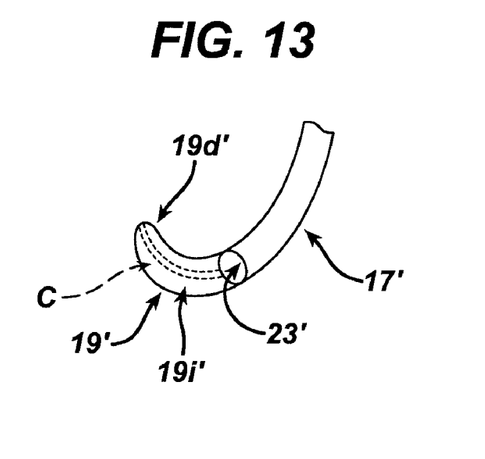
FIG. 13 is a side partial view of one embodiment of a device having a curved, non-cannulated distal tip.

FIG. 13 illustrates another exemplary embodiment of a curved distal tip 19' configured similar to the curved distal tip 19 but including a non-cannulated curved member. The curved distal tip 19' can have a variety of sizes, shapes, and configurations. As shown, the curved distal tip 19' be configured similar to a shoe horn and have a curved surface distally extending from the elongate body 17' with a tapered distal end 19d'. An interior surface 19i' of the curved distal tip 19' can be in communication with the passageway 23' such that a surgical tool advanced through the passageway 23' can come into contact with the interior surface 19i' and be guided thereal-ong. The interior surface 19i' can optionally include a longitudinal channel C, e.g., a c-shaped depression, formed therein configured to seat a surgical tool therein to help more effectively guide the surgical tool along the degree of curvature of the curved distal tip 19'. Although only one channel C is shown in the curved distal tip 19', the curved distal tip 19' can include multiple channels, e.g., first and second channels to respectively seat first and second terminal ends of a guide wire. Further, although the channel C is shown in FIG. 13 as formed only in the curved distal tip 19', the channel C can extend along a full or partial length along a sidewall of the elongate body 17' to help guide a surgical tool therethrough. The channel C can also extend along a full or partial length of the curved distal tip 19'. The curved distal tip 19' can be removably or fixedly attached to an elongate body 17' similar to the elongate body 17 of FIG. 6 and having a longitudinal inner passageway 23' extending therethrough. Alternatively, the elongate body 17' can be non-cannulated similar to the curved distal tip 19' and instead guide a surgical tool using a track or channel similar to the channel C. In use, a surgical tool (not shown) can be advanced in a distal direction through the inner passageway 23' of the elongate body 17' and be guided in a curved direction along the curved distal tip 19' similar to that discussed above regarding the device 11. A device including the curved distal tip 19' can optionally be mounted to an overtube similar to the overtube 41 discussed above.

Figure 14:
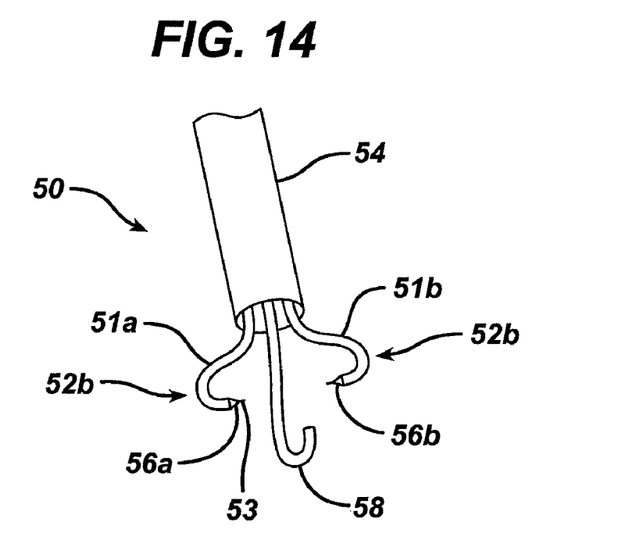
FIG. 14 is a perspective view of a distal end of one embodiment of a guide wire device including a plurality of curved distal tips advanced with an endoscope through an outer sheath.

A surgical device can include any number of curved distal tips configured to be positioned in an opening in a tissue wall and configured to guide at least one surgical tool in an arcuate path around a hollow body organ or conduit, within a hollow body organ or conduit, and/or around any other body tissue. FIG. 14 illustrates one exemplary embodiment of a surgical device 50 having a plurality of manipulable arms 51a, 51b having respective curved distal tips 52a, 52b. The device 50 and the curved distal tips 52a, 52b can be configured similar to the device and the curved distal tips discussed above. The device can also be configured as described in previously mentioned U.S. Patent Publication No. 2009/0005797 entitled "Methods And Devices For Placement Of An Intra-Abdominal Or Intra-Thoracic Appliance Through A Natural Body Orifice" filed Apr. 22, 2008, U.S. Pat. No. 6,494,888 entitled "Tissue Reconfiguration" issued Dec. 17, 2002, and U.S. Pat. No. 6,663,639 entitled "Methods And Devices For Tissue Reconfiguration" issued Dec. 16, 2003.

The device 50 can be used in any surgical procedure, as mentioned above. In an exemplary embodiment, the device 50 can be used for placement of a guide wire 53 and an appliance, e.g., a gastric band. As shown in this embodiment, an outer tube or sheath 54 can be used to deliver the device 50 through the esophagus and pyloric valve into the stomach, with a scoping device such as an endoscope 58 being optionally advanced through a working channel of the device 50. The manipulable arms 51a, 51b can include tissue piercing elements 56a, 56b at each distal end and can be hollow to permit delivery of the guide wire 53. Using the device 50, appropriate locations on the organ wall can be visualized with the endoscope 58 and pierced by the tissue piercing elements 56a, 56b on the manipulable arms 51a, 51b. The guide wire 53 can then be advance through the organ wall and around the outer surface of the organ. Upon return to the exit opening or a secondary opening created by piercing elements 56a, 56b, the guide wire 53 can be recaptured by the manipulable arms 51a, 51b, or an another device, such as a grasper arm inserted through the tube 54. With the end of the guide wire 53 recaptured, it can be returned external to the hollow organ (and patient), and the appliance can be guided into place therewith.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam, and a liquid bath (e.g., cold soak).

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety

What is claimed is:

1. A surgical method, comprising:
   advancing a guide element having a curved distal tip into a hollow body organ;
   positioning the guide element through an opening formed through a wall of the body organ with a proximal portion of the guide element positioned inside the body organ and a distal portion of the guide element outside the body organ with the curved distal tip curving along at least a portion of an outer surface of the body organ;
   advancing a surgical tool through the opening and along the curved distal tip to guide the surgical tool along the outer surface of the body organ;
   advancing the surgical tool around a perimeter of the body organ; and
   advancing the surgical tool back through the opening to position first and second lengths of the surgical tool inside the body organ with a third length of the surgical tool between the first and second lengths extending around the perimeter of the body organ.

2. The method of claim 1, further comprising advancing a restriction band over the third length of the surgical tool to position the restriction band around the perimeter of the body organ.

3. The method of claim 1, wherein the guide element comprises an elongate tubular body, and advancing the surgical tool along the curved distal tip comprises advancing the surgical tool through the elongate tubular body.

4. The method of claim 1, wherein positioning the guide element through the opening comprises manipulating a control mechanism to change an angle that the distal portion of the curved distal tip curves toward the outer surface of the body organ.

* * * * *